United States Patent [19]

Kang

[11] Patent Number: 4,916,754
[45] Date of Patent: Apr. 17, 1990

[54] ANTIGLARE APPARATUS

[76] Inventor: Hyung B. Kang, 18122 Santa Cecilia Dr., Fountain Valley, Calif. 92708

[21] Appl. No.: 302,384

[22] Filed: Jan. 27, 1989

[51] Int. Cl.⁴ ............................................. A61F 9/04
[52] U.S. Cl. ........................................... 2/12; 2/432
[58] Field of Search ...................... 2/12, 432, 10, 171, 2/453, 199

[56] References Cited

U.S. PATENT DOCUMENTS

| | | | |
|---|---|---|---|
| 593,374 | 11/1897 | Gibson | 2/10 |
| 1,152,431 | 9/1915 | Mullen | 2/12 |
| 1,199,650 | 9/1916 | Aman | 2/10 |
| 1,716,719 | 6/1929 | Christopher | 2/10 |
| 2,530,881 | 11/1950 | Houston | 2/12 |
| 2,545,078 | 3/1951 | Gardner | 2/432 X |
| 2,556,433 | 6/1951 | Mitchell | 2/432 |
| 3,466,664 | 9/1969 | Militello | 2/171 |
| 4,724,546 | 2/1988 | Cumbie, Jr. | 2/12 |
| 4,837,862 | 6/1989 | Heil | 2/12 |

*Primary Examiner*—Peter Nerbun
*Attorney, Agent, or Firm*—Richard C. Litman

[57] ABSTRACT

A dual visor system enables the wearer to use the device as a conventional visor, or to lower a secondary visor to a position below the eyes to provide an aperture to reduce both direct and reflected light entering the wearer's eyes. By providing a roughened upper surface on the lower visor, reflection and glare is further reduced. Both primary and secondary visors may be formed of either opaque or translucent materials in order to either block or reduce light passage to the eyes as desired.

4 Claims, 2 Drawing Sheets

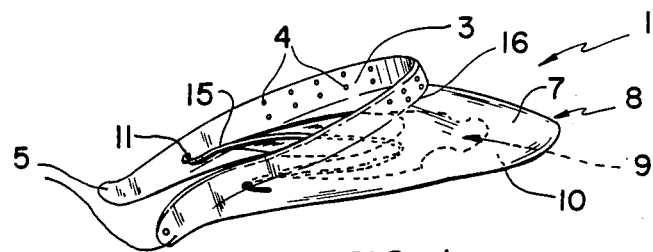
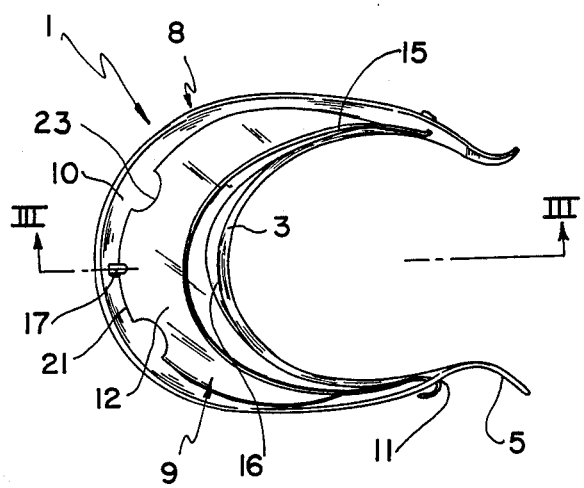
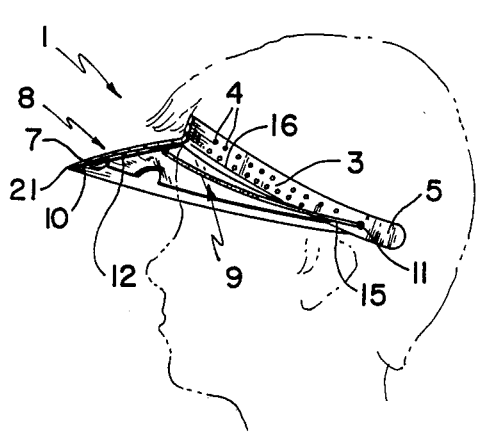
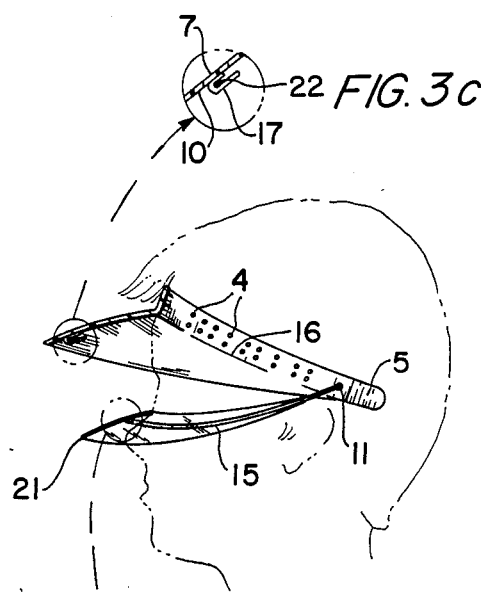
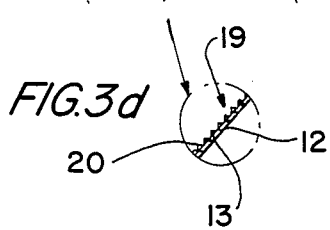

ANTIGLARE APPARATUS

FIELD OF THE INVENTION

This invention relates generally to headwear, and more specifically to headwear for the protection of the eyes and face against glare.

BACKGROUND OF THE INVENTION

Numerous attempts to provide adequate protection against glare from the sun have been made. While these attempts have yielded many devices which may be suitable under some conditions, a number are unable to provide the necessary versatility often necessary.

An example is U. S. Pat. No. 2,556,433, which discloses an antiglare eye protective device. While such a device may block a portion of the light which would otherwise enter the wearer's eyes, by its translucent nature it is incapable of completely shielding the wearer's eyes when used as a visor.

U. S. Pat. No. 4,724,546 discloses a visor with a movable light shield. This device is intended to reduce the light and any associated harmful rays which might enter the eyes. However, many such devices allow wavelengths of light potentially more damaging, such as ultraviolet, to pass without reduction. As the pupil of the eye responds only to visible light it will tend to open as such visible light is reduced upon passage through such a shield, thereby allowing even greater quantities of harmful wavelengths of light to enter the eye than if no protection were Worn at all.

None of the above noted patents are seen to disclose the specific arrangement of concepts disclosed by the present invention.

SUMMARY OF THE INVENTION

By the present invention, an improved antiglare apparatus comprising a variable position dual visor system is disclosed.

Accordingly, one of the objects of the present invention is to provide an antiglare device which will block the harmful rays of the sun without obstructing vision.

An additional object of the present invention is to provide a device which is easily convertible from a conventional visor to a device which provides greater protection against harmful light.

Another object of the present invention is to provide a functional device which is lightweight and aesthetically pleasing.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

FIG. 1 is a perspective view of the apparatus.

FIG. 2 is a plan view of the bottom of the apparatus.

FIG. 3a is a cross sectional view taken at line III—III of the apparatus with the secondary visor in the stored position.

FIG. 3b is a cross sectional view taken at line III—III of the apparatus with the secondary visor lowered.

FIG. 3c is a cross sectional view of the locking means for the secondary visor.

FIG. 3d is a cross sectional view of the secondary visor disclosing the antiglare means.

Similar reference characters designate corresponding parts throughout the several figures of the drawings.

DESCRIPTION OF THE PREFERRED EMBODIMENT

Figure 4A:
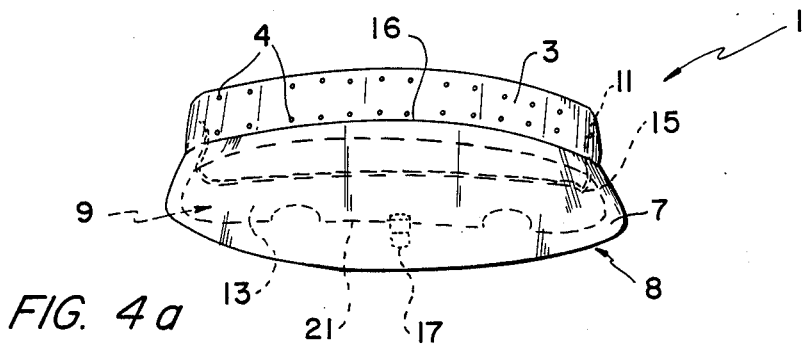
FIG. 4a is a frontal view of the apparatus.
Figure 4B:
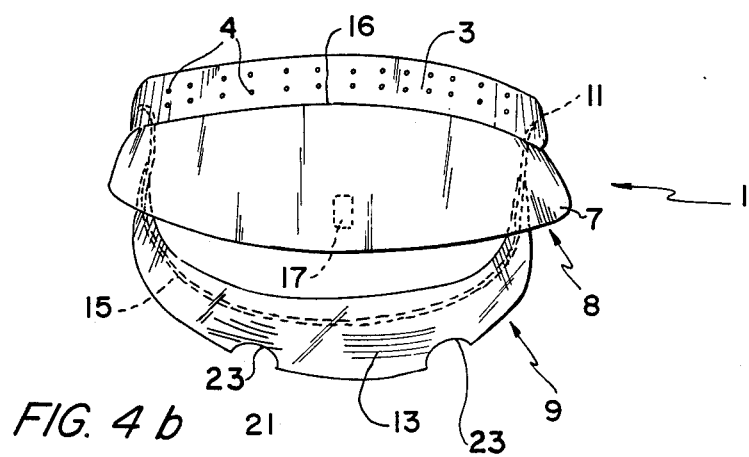
FIG. 4b is a frontal view displaying the secondary visor lowered.

Referring to the drawings, the antiglare apparatus, generally designated 1, is based upon a previously known conventional visor. The apparatus is preferably formed of a flexible material such as plastic or the like, in order to more easily conform to the variety of shapes of the heads of various users. The apparatus is symmetrical about the axis III—III. The support for apparatus 1 is provided by band 3 which contacts the forehead of the wearer. The periphery of band 3 imitates the shape of the perimeter of the human head in the forehead temple region. Band 3 also incorporates perforations 4 to provide ventilation and to aid in the evaporation of perspiration while in use. Located at each end of band 3 are indents 5 which through their curved shape apply pressure to secure the apparatus to the wearer's head.

Attached to band 3 is primary visor 8 which extends essentially horizontally away from the head. Primary visor 8 forms a crescent shape and contacts the band 3 along the entire lower edge 16 of band 3. Primary visor 8 comprises an upper surface 7 and a lower surface 10. Primary visor 8 is of sufficient surface area and extends at such a distance from band 3 to provide adequate shading of light sensitive parts of the wearer's face. Primary visor 8 is provided with a curved outer edge opposite its attachment at band 3.

Secondary visor 9 is of a crescent shape similar to that of primary visor 8. Secondary visor 9 comprises an upper surface 13 and a lower surface 12. Upper surface 13 conforms to the shape of the lower surface 10 of primary visor 8. Upper surface 13 includes ridging 19 which resembles a triangular shape. The long sides 20 of the triangular ridges 19 face away from the eyes in order to provide an additional means to reflect light away from the eyes. Secondary visor 9 is pivotally attached to band 3 by support members 15. The support members 15 extend from the ends of secondary visor 9 and are received in receptacles 11. Secondary visor 9 is storable by engaging upper surface 13 with the lower surface 10 of primary visor 8. The storage position is maintained by a locking tab 17 which holds secondary visor 9 in place relative to primary visor 8, as described below.

The lower surface 10 of primary visor 8 contains a locking tab 17 which may engage secondary visor 9. Locking tab 17 provides support to retain secondary visor 9 in the storage position. The storage position mates the upper surface 13 of secondary visor 9 with the lower surface 10 of primary visor 8. Locking tab 17 is permanently affixed to the lower surface 10 of primary visor 8 so as to engage the forward edge or lip 21 of secondary visor 9 when secondary visor 9 is resting in its stored position. The lip 21 of secondary visor 9 fits into notch 22 of locking tab 17. In order to allow secondary visor 8 to be more easily grasped and released from its stored position, indentations 23 are formed in the lip 21 of secondary visor 8 on either side of centerline III—III.

In use, secondary visor 9 is released from the locking tab 17 and lowered to the operable position, in which secondary visor 9 rests upon the nose of the wearer as shown in FIG. 3b. With primary visor 8 in fixed position and secondary visor 9 lowered, the amount of light which enters the eyes is reduced, as light reflected from the surface is blocked by secondary visor 9. Also, because of the ridges 19 on the upper surface 13 of secondary visor 9, light which enters through the aperture formed between primary visor 8 and secondary visor 9 is partially reflected. Thus, the apparatus may be used as a conventional visor, or if greater protection from light, especially surface glare, is desired the secondary visor 9 may be lowered.

It is to be understood that the present invention is not limited to the sole embodiment described above, but encompasses any and all embodiments within the scope of the following claims.

What is claimed is:

1. An antiglare visor comprising:

an engaging band including a periphery which conforms to the shape of the forehead and providing for attachment to the wearer by pressure fit above each ear, a primary visor with upper and lower surfaces which is attached to said engaging band and projects outward from same to provide shade for the face of the wearer, a secondary visor with upper and lower surfaces and a forward edge which is pivotally attached to said engaging band, said secondary visor is storable on said lower surface of said primary visor, said primary visor having on said lower surface retaining means to grip said forward edge of said secondary visor, said secondary visor is downwardly movable from said primary visor lower surface upon disengagement with said retaining means to rest upon the nose of the wearer thereby providing an aperture between said upper and lower visors, whereby both direct and reflected light are reduced.

said upper surface of said secondary visor is provided a ridged contour to reflect light away from the wearer's eyes, said forward edge of said secondary visor having a plurality of indentations allowing grasping of said secondary visor by the fingers of the wearer for removal of said secondary visor form said retaining means.

2. An antiglare device according to claim 1 wherein, said primary and secondary visors in addition to said engaging band are fabricated from a flexible material.

3. An antiglare visor according to claim 1 wherein, said primary visor blocks the transmission of light.

4. An antiglare visor according to claim 1 wherein, said engaging band includes a plurality of ventilation holes passing completely therethrough.

* * * * *